(12) United States Patent
Bousquet et al.

(10) Patent No.: US 9,699,417 B2
(45) Date of Patent: Jul. 4, 2017

(54) DEVICE FOR SEARCHING FOR DEFECTS ON PARTS BY ENDOSCOPY

(75) Inventors: Sadia Bousquet, Moissy Cramayel (FR); Pascal Cendrier, Boussy Saint Antoine (FR); Jean-Claude Lemoal, La Brosse Hericy (FR); Jean Rovegno, La Ciotat (FR)

(73) Assignee: SNECMA, Paris (FR)

(*) Notice: Subject to any disclaimer, the term of this patent is extended or adjusted under 35 U.S.C. 154(b) by 371 days.

(21) Appl. No.: 14/000,014

(22) PCT Filed: Feb. 28, 2012

(86) PCT No.: PCT/FR2012/050411
§ 371 (c)(1),
(2), (4) Date: Aug. 16, 2013

(87) PCT Pub. No.: WO2012/117196
PCT Pub. Date: Sep. 7, 2012

(65) Prior Publication Data
US 2013/0321612 A1    Dec. 5, 2013

(30) Foreign Application Priority Data

Feb. 28, 2011 (FR) .................................... 11 51616
Mar. 15, 2011 (FR) .................................... 11 52123

(51) Int. Cl.
*G01N 7/00* (2006.01)
*H04N 7/18* (2006.01)
(Continued)

(52) U.S. Cl.
CPC ............... *H04N 7/18* (2013.01); *F01D 5/005* (2013.01); *F01D 25/285* (2013.01); *G01N 21/91* (2013.01);
(Continued)

(58) Field of Classification Search
CPC ................................ H04N 7/18; G01N 21/91
(Continued)

(56) References Cited

U.S. PATENT DOCUMENTS 4,483,326 A * 11/1984 Yamaka ............... A61B 1/0057
                                                                600/141
4,995,872 A *  2/1991 Ferrara ............. A61M 25/0113
                                                                604/264
(Continued)

FOREIGN PATENT DOCUMENTS

EP      1 494 060      1/2005
GB      2 474 834      5/2011

OTHER PUBLICATIONS

International Search Report Issued Aug. 22, 2012 in PCT/FR12/050411 Filed Feb. 28, 2012.

*Primary Examiner* — Jeffery Williams
(74) *Attorney, Agent, or Firm* — Oblon, McClelland, Maier & Neustadt, L.L.P.

(57) ABSTRACT

A device for searching for defects on parts that are masked, such as turbine engine blades, the device including a tubular sheath, a light-guide guiding light, an image-transmission mechanism transmitting images housed inside the sheath, an examination head at a distal end of the sheath including an illumination mechanism and an image-taking mechanism connected to the light-guide and to the image-transmission mechanism housed in the sheath, a mechanism spraying a succession of penetrant test materials on the part for inspection including a capillary slidably guided in a duct housed in the sheath, and a mechanism adjusting orientation of the examination head at the distal end of the sheath.

16 Claims, 7 Drawing Sheets

(51) Int. Cl.
| | |
|---|---|
| *F01D 5/00* | (2006.01) |
| *F01D 25/28* | (2006.01) |
| *G01N 21/91* | (2006.01) |
| *G01N 21/954* | (2006.01) |
| *G02B 23/24* | (2006.01) |

(52) U.S. Cl.
CPC ....... *G01N 21/954* (2013.01); *G02B 23/2476* (2013.01); *F05D 2260/80* (2013.01); *G02B 23/2469* (2013.01)

(58) Field of Classification Search
USPC .......................................................... 348/82
See application file for complete search history.

(56) References Cited

U.S. PATENT DOCUMENTS

| | | | | |
|---|---|---|---|---|
| 5,115,136 | A | * | 5/1992 | Tomasch ............ G01N 21/8803 250/302 |
| 5,644,394 | A | * | 7/1997 | Owens ................... B23P 6/002 15/324 |
| 8,910,359 | B2 | * | 12/2014 | Jones ..................... G01N 21/91 29/402.01 |
| 2003/0217430 | A1 | * | 11/2003 | Montgomery ...... A47L 11/4061 15/321 |
| 2005/0041097 | A1 | | 2/2005 | Bernstein et al. |
| 2005/0128288 | A1 | | 6/2005 | Bernstein et al. |
| 2005/0200842 | A1 | | 9/2005 | Bonningue et al. |
| 2007/0135776 | A1 | * | 6/2007 | Yamamoto ............ A61M 31/00 604/289 |
| 2008/0297785 | A1 | | 12/2008 | Bonningue et al. |

* cited by examiner

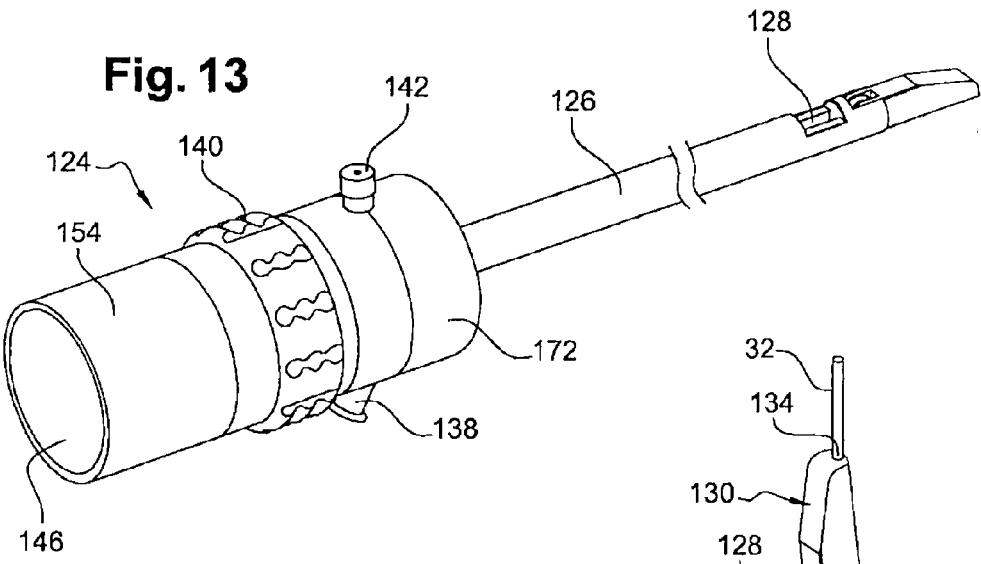
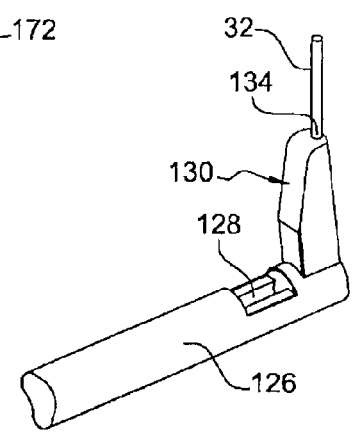
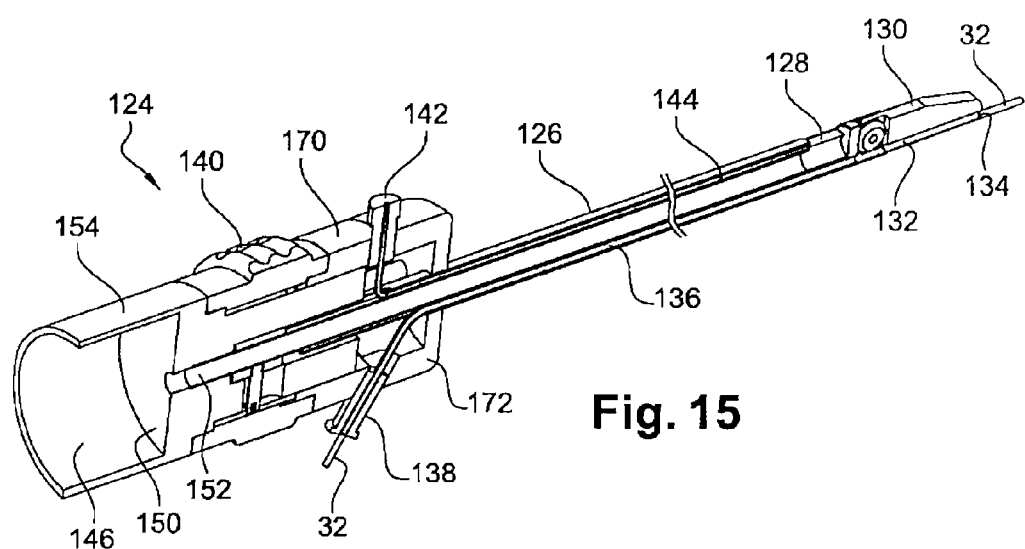

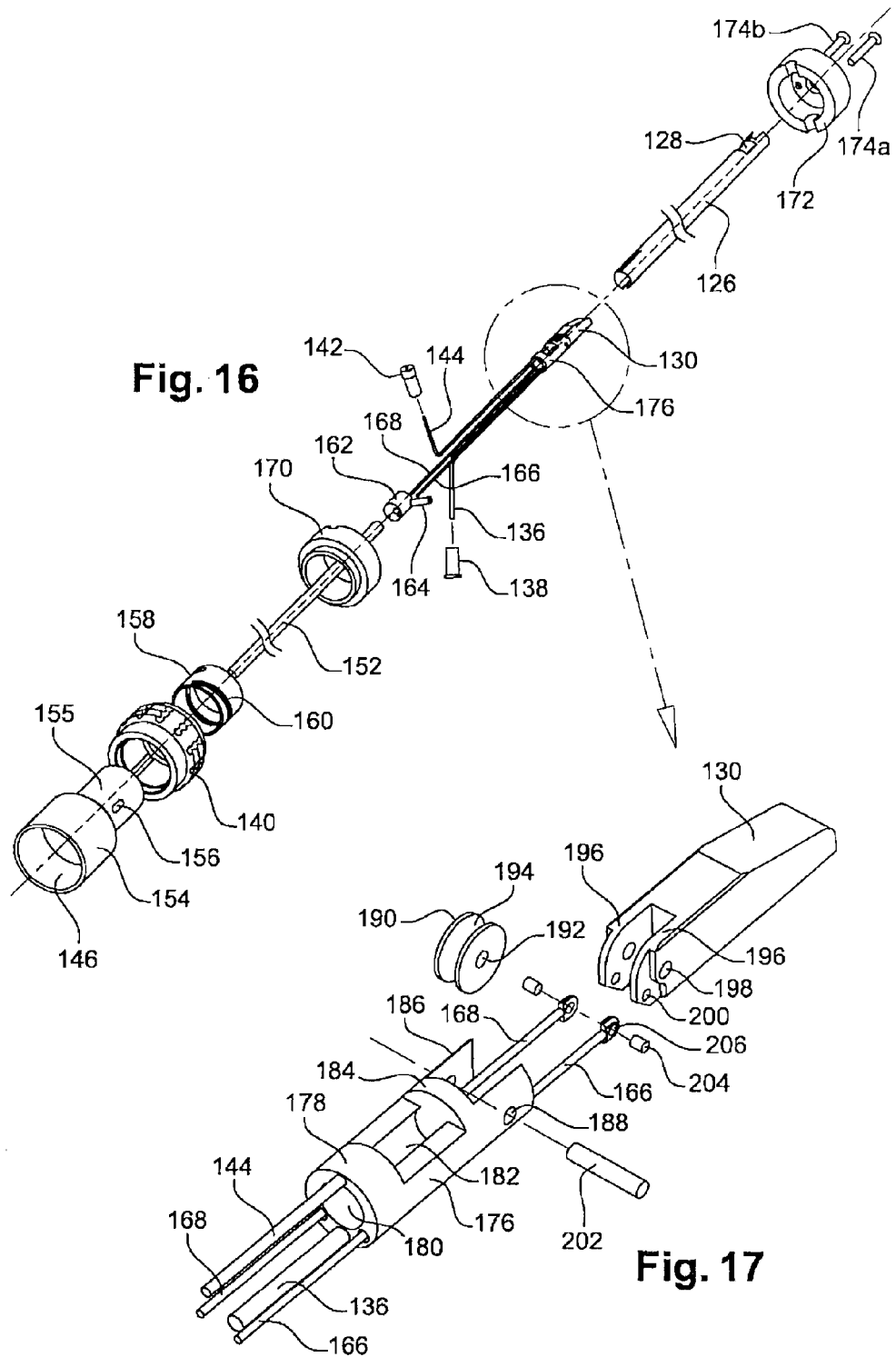

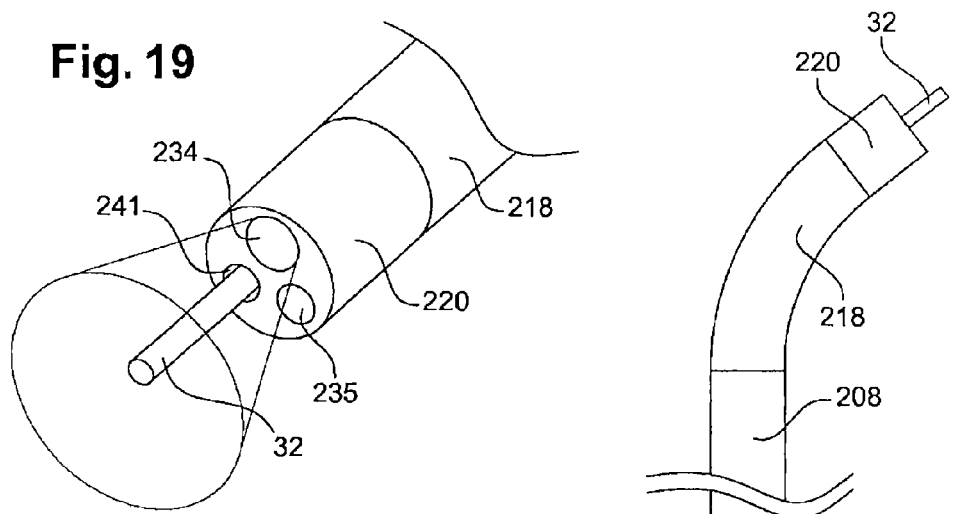
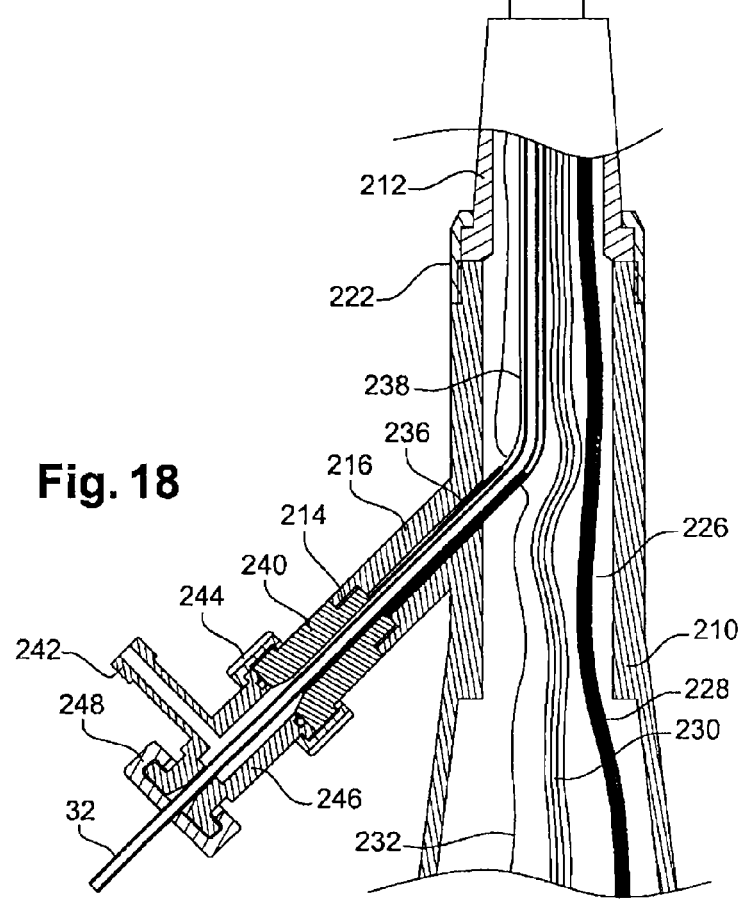

DEVICE FOR SEARCHING FOR DEFECTS ON PARTS BY ENDOSCOPY

BACKGROUND OF THE INVENTION

Field of the Invention

The invention relates to a device for using endoscopy to search for defects on parts that are masked, i.e. that are not directly visible, e.g. such as parts inside a turbine engine.

Description of the Related Art

It is known to inspect the internal components of equipment or of a machine with the help of an endoscope which is an elongate optical instrument of small diameter that is passed through a small orifice in a wall in order to examine the appearance of components that are to be found on the other side of the wall. The endoscope can thus be used for inspecting blades of a turbine engine such as an airplane turboprop or turbojet without it being necessary to disassemble the engine.

In order to view defects of a part, it is known to use a penetrant test technique that consists in depositing organic materials on the surface under examination of the part and in observing under ultraviolet illumination the extent to which the organic materials impregnate the surface of the part. The presence of defects is revealed after drying the surface of the part and depositing a developer material that reveals the organic material that has infiltrated into surface defects of the part when the part is illuminated with ultraviolet light.

In order to facilitate the use of the penetrant testing technique on an airplane engine while it is attached under the wing of an airplane, proposals have already been made in document U.S. Pat. No. 4,273,110 to use an endoscope incorporating penetrant test means. For that purpose, the proposed instrument comprises an elongate rigid cylindrical sheath of small diameter containing a duct that is used for passing means for guiding ultraviolet light and visible light towards an end of the instrument that is close to the part for inspection. The instrument also has an optical duct for integrating means for transmitting and forming images in order to observe the illuminated zone, and a plurality of ducts, each used for passing a respective penetrant test material.

That type of instrument is relatively easy to use when it is desired to examine a masked part, i.e. a part that is not directly visible and that is situated behind a wall. For that purpose, it suffices to insert the rigid sheath through an orifice in the wall and to perform the inspection in the manner described above. The Applicant has also made proposals in a prior application FR 2 857 094 to perform the penetrant testing and the observation with the help of two separate endoscopes. In another prior application, FR 2 861 185, the Applicant proposes using an endoscope with ultraviolet illumination and deflected distal viewing, the endoscope having a rigid tubular body.

Nevertheless, those prior devices require a plurality of independent ducts for passing different penetrant test materials, thereby requiring the endoscope to have a section that is large and restricting its use to orifices or passages that are sufficiently large.

BRIEF SUMMARY OF THE INVENTION

A particular object of the invention is to provide a solution to that problem that is simple, satisfactory, and inexpensive.

To this end, the invention provides a device for searching for defects on parts that are masked and accessible via a passage that is not rectilinear inside a turbine engine such as an airplane turboprop or turbojet, the device comprising a tubular sheath and light-guide means for guiding light and image-transmission means for transmitting images housed in the sheath in order to illuminate and observe a part for inspection, the device being characterized in that it comprises an examination head at the distal end of the sheath, the head having illumination means and image-taking means connected to the light-guide means and to the image-transmission means housed in the sheath, means for spraying a succession of penetrant test materials on the part for inspection, said means comprising a capillary slidably guided inside a duct housed in the sheath, and in that it includes means for adjusting the orientation of the examination head at the distal end of the sheath.

Integrating a duct inside the sheath makes it possible to insert and withdraw a capillary for passing a penetrant test material, which capillary is mounted to slide inside the duct, thus making it possible to use a plurality of capillaries in succession, each capillary being dedicated to pass one particular penetrant test material. The diameter of the tubular sheath can thus be smaller than the diameter of a prior art sheath.

Slidably inserting the capillary inside the duct also makes it possible to bring the distal end of the capillary close to the zone of the part where it is desired to apply the penetrant test material. In this manner, the illumination means and the image-taking means may be set back from the distal end of the capillary. This avoids penetrant test material spray from becoming deposited on the illumination means or on the image-taking means. When the operator desires to observe the treated region, the operator pulls on the proximal portion of the capillary in order to bring its distal end closer to the distal end of the sheath.

According to another characteristic of the invention, the device comprises air-blow means for blowing air on the illumination means and image-taking means located at the distal end of the sheath.

The air-blow means prevent the illumination means and the image-taking means from being polluted by the various penetrant test materials injected via the dedicated capillaries that are inserted in succession into the duct.

In a particular embodiment of the air-blow means, they comprise means for feeding air under pressure that are connected to a blow tube leading at its distal end to the vicinity of the illumination means and the image-taking means.

In a preferred embodiment of the invention, the means for feeding air under pressure are connected to the proximal end of the duct for passing the capillary in order to feed the duct with a continuous stream of air that leaves via its distal end.

In operation, the stream of air that blows continuously between the inside surface of the duct and the capillary prevent drops of penetrant test materials such as acetone, a penetrant dye, an emulsifier, or a developer, or indeed washing water, from becoming deposited inside the duct.

According to another characteristic of the invention, the proximal end of the flexible sheath is connected to a handle for fastening to the engine and the duct housing the capillary is extended inside the handle and is connected to a rigid tube carried by the handle and serving to insert the capillary into the inside of the duct.

According to another characteristic of the invention, the device comprises holder means for preventing the capillary from sliding inside the duct, constituted by an endpiece designed to be engaged and held against the free end of the rigid tube, the endpiece having means for clamping onto the capillary by pinching it.

In a particular embodiment of the invention, the endpiece includes a passage leading to the inside of the tube and forming an inlet for connection to the means for feeding air under pressure.

In this configuration, the endpiece with the clamping means also serves to make a connection with the means for feeding air under pressure.

According to another characteristic of the invention, the orientation adjustment means comprise a control member for controlling the angular orientation of the examination head, which member is rotatably mounted on the endoscope handle and is connected to transmission means for transmitting the orientation control to the examination head, these transmission means being housed in the sheath.

Turning the control member in one direction or the other serves to cause the examination head to tilt relative to the remainder of the sheath.

In a particular embodiment of the invention, the means for adjusting the orientation of the examination head comprise at least two cables guided inside the sheath and fastened at their distal ends to the examination head at two diametrically opposite points, and wound under tension at their proximal portions in opposite directions on a rotary control member situated on the handle.

In another particular embodiment of the invention, the means for transmitting the orientation control comprise at least one rod extending inside the sheath and connected at its distal end to a mechanism for converting rotary movement of the ring into movement in translation of the rod, the rod being connected by its distal end to a finger that is pivotally hinged to the distal end of the sheath about an axis that is perpendicular to the sheath.

Advantageously, the distal finger includes an axial channel for passing the capillary and is hinged to pivot between a position in which it is in alignment with the axis of the sheath and a position in which it is oriented perpendicularly to the axis of the sheath.

The pivoting of the hinge finger induces pivoting of the distal end of the capillary, thereby enabling the distal end of the capillary to be oriented angularly in three dimensions in order to spray the penetrant test materials on the part for inspection.

In a preferred configuration of the invention, the tubular sheath is flexible and the capillary is flexible, thereby making it possible to perform non-destructive inspection of a part that is to be found inside a complex three-dimensional structure and that is accessible solely via a narrow and non-rectilinear passage, where this is not possible using an endoscope of rigid structure.

According to another characteristic of the invention, the distal end of the sheath is fitted with a spray endpiece at its distal end.

Preferably, the spray endpiece at the distal end of the capillary is removable and can be selected from a set of spray endpieces for spraying radially, forwards, or backwards.

In a practical embodiment of the invention, the sheath is of circular section with a diameter lying in the range 6 millimeters (mm) to 10 mm, and the duct for passing the capillary has a diameter of about 1.2 mm, the capillary having a diameter of about 0.8 mm.

According to another characteristic of the invention, the device has fastener means for fastening to a portion of the engine, which means comprise a hinge arm connected to the handle.

The invention also provides a method of non-destructively inspecting a masked part inside a three-dimensional structure by means of the above-described device, the method consisting in:
- inserting and guiding the examination head inside a three-dimensional structure to a position for examining the part for inspection;
- with the examination head placed facing the part for inspection, feeding the proximal end of the capillary with a first penetrant test material and applying this material via the distal end of the capillary to the part for inspection;
- slidably withdrawing the capillary from the duct in which it is housed; and
- slidably inserting a second capillary into the duct and bringing its distal end into the vicinity of the part for inspection, and then feeding the proximal end of the second capillary with a second penetrant test material and applying the second material to the part for inspection.

BRIEF DESCRIPTION OF THE SEVERAL VIEWS OF THE DRAWINGS

Other advantages and characteristics of the invention appear on reading the following description made by way of non-limiting example and with reference to the accompanying drawings, in which:

FIGS. 11 to 13 are perspective views of endoscopic equipment having a rigid inspection tube and adapted to penetrant testing under ultraviolet illumination in an embodiment of the invention;

FIG. 14 is a perspective view of the distal end of the endoscope of FIGS. 11 to 13;

FIG. 15 is a view in perspective and in longitudinal section of the endoscope of FIGS. 11 to 13;

FIG. 16 is an exploded perspective view of the endoscope of FIGS. 11 to 13;

FIG. 17 is an exploded perspective view of the distal end of the endoscope of FIGS. 11 to 13;

FIG. 18 is a diagrammatic fragmentary axial section view of an endoscope in a variant embodiment of the invention; and FIG. 19 is a perspective view of the distal end of the FIG. 18 endoscope.

DETAILED DESCRIPTION OF THE INVENTION

Figure 1:
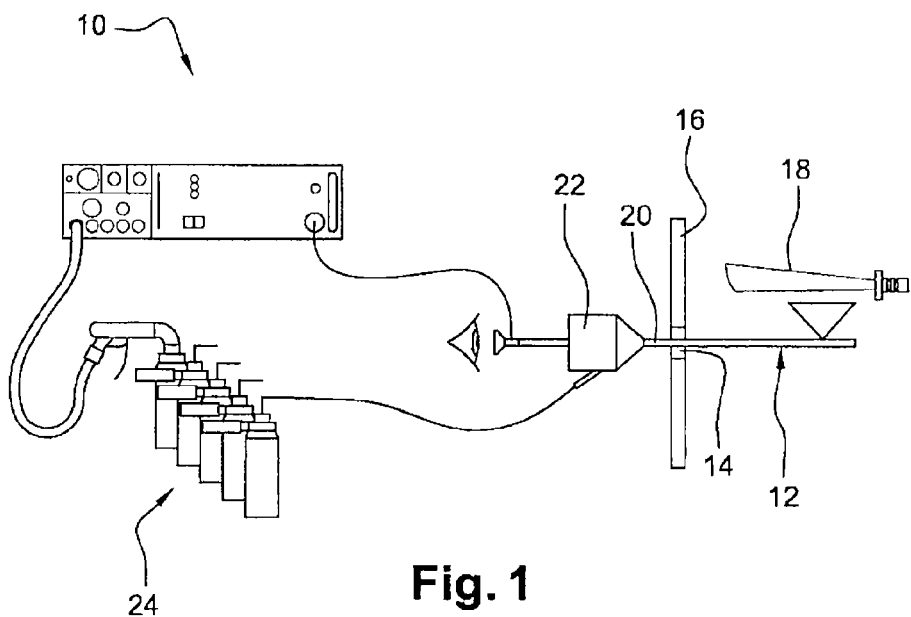
FIG. 1 is a diagrammatic view of a prior art device for searching for defects.

Reference is made initially to FIG. 1, which shows a prior art device 10 for searching for defects, the device comprising a rigid tubular cylindrical stick 12 for inserting via one end into an endoscopic orifice 14, e.g. made in a wall of a casing 16 of a turbine engine within which there is a part 18 that is to be examined, such as a rotor blade, for example.

The cylindrical stick 12 has a duct receiving means for guiding light and for transmitting images in order to illuminate and observe the part. The cylindrical stick 12 also has a duct for spraying penetrant test materials, such as acetone, a penetrant dye, an emulsifier, or water. The end 20 of the stick 12 opposite from its end for inserting in the orifice 14 is connected via a circuit 22 to means 24 for feeding it with penetrant test materials and to illumination and control means.

This type of device requires the use of a plurality of independent ducts for passing the various penetrant test materials, thereby increasing the diameter of the endoscope and limiting its use to endoscopic orifices or passages that are sufficiently large.

Figure 2:
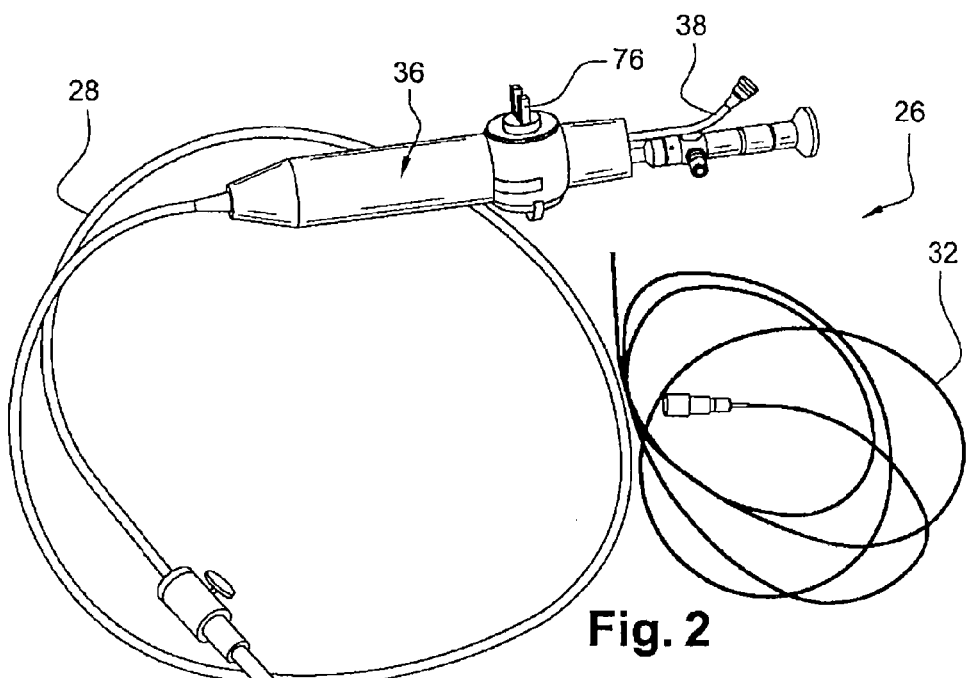
FIG. 2 is a diagrammatic perspective view of a device of the invention for searching for defects.
Figure 3:
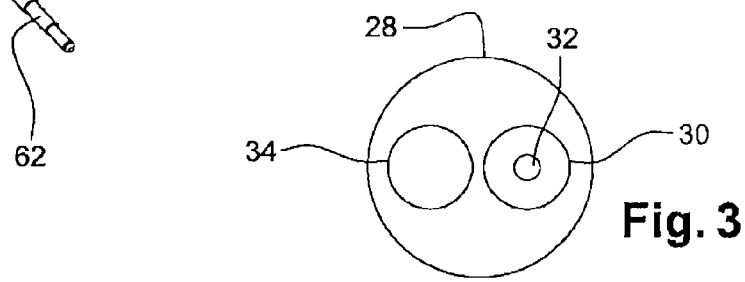
FIG. 3 is a diagrammatic section view of the flexible sheath of the device of the invention.

The device 26 of the invention provides a solution to that difficulty by replacing the rigid cylindrical stick with a flexible sheath 28 including an orientable examination head 62 and incorporating a duct 30 in the sheath 28, which duct houses a capillary 32 slidably engaged inside the duct 30 (FIGS. 2 and 3). FIG. 3 also shows a second duct 34 used for passing light-guide means and image-taking and image-transmission means. These means are described in greater detail below.

The device has an endoscope handle 36 of substantially cylindrical shape with a first end that is connected to the proximal end of the flexible sheath 28. The second end of the handle 36 carries a bent rigid tube 38 leading to the inside of the handle 36 and communicating with the duct 30 housing the capillary 32.

The device 26 has means for holding the capillary 32 stationary inside the duct 30. In a particular embodiment (FIGS. 4 and 5), these means comprise an endpiece 40 with a cylindrical or frustoconical skirt 42 engaged and clamped on the free end of the rigid tube 38.

Figure 4:
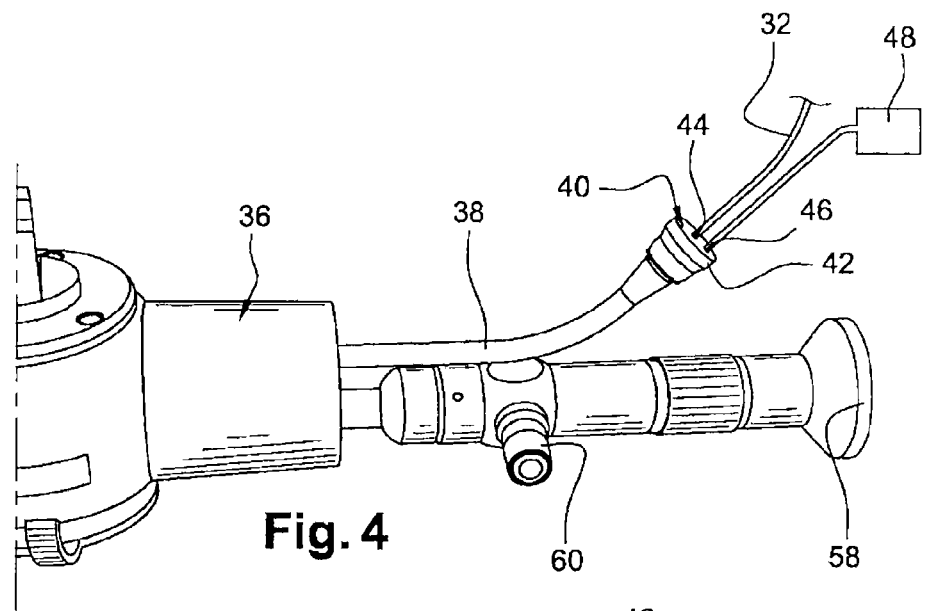
FIG. 4 is a diagrammatic perspective view on a larger scale of the proximal portion of the FIG. 2 device.
Figure 5:
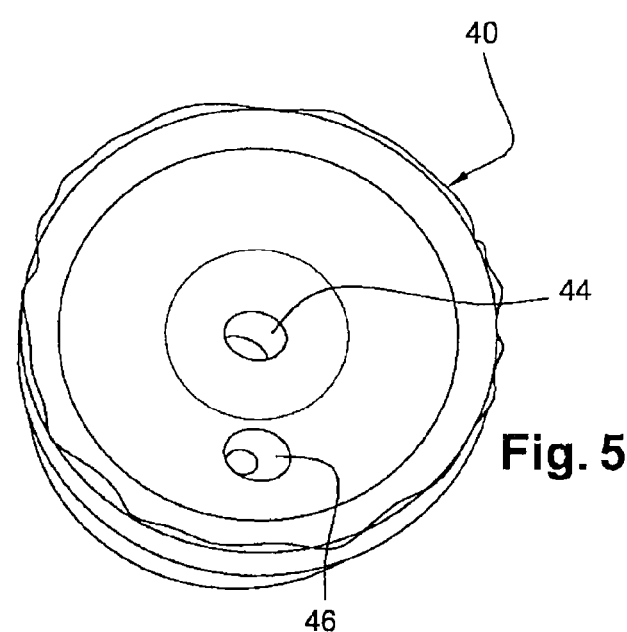
FIG. 5 is a diagrammatic end view of an endpiece having inserted therein a capillary for passing a penetrant test material.

The endpiece 40 has a central orifice 44 enabling a capillary 32 to be inserted inside the rigid tube 38 and consequently inside the duct 30 extending inside the flexible sheath 28 (FIGS. 3 and 4). The endpiece 40 includes means for clamping the capillary 32 in such a manner as to prevent the capillary 32 from moving relative to the endpiece 40. By way of example, these means are made by dimensioning the diameter of the orifice 44 so that it is slightly smaller than the outside diameter of the capillary 32. Thus, the capillary can be moved manually to slide inside the tube 38 and each time the operator lets go of the capillary 32, the capillary is held in position. In order to enable such clamping, the endpiece 40 is made of a suitable plastics or elastomer material, such as rubber, for example.

The device of the invention also has air-blow means for blowing air from the distal end of the sheath. For this purpose, the endpiece 40 includes a second orifice 46 formed in its front face and leading to the inside of the rigid tube 38.

This orifice 46 is connected to means 48 for feeding air under pressure and enabling the tube 38 and the duct 30 to be fed with a continuous stream of air 50 that leaves via the distal end of the duct 30. The exiting stream of air thus prevents the inside of the duct 30 becoming polluted with drops of the various penetrant test materials (FIG. 5) and it limits the spraying of penetrant test materials in the vicinity of the illumination means and the image-taking means formed at the distal end of the sheath.

When the pressure of the stream of air is at least 0.3 bars, it is possible to dry the part with the air feed means, e.g. between two successive applications of different penetrant test materials.

Figure 6:
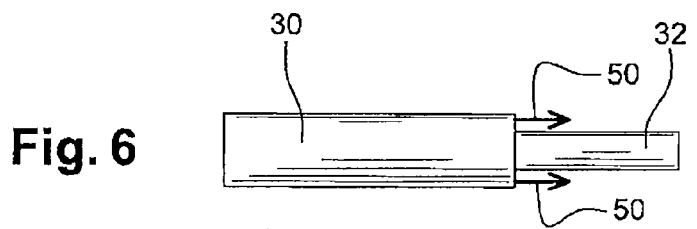
FIG. 6 is a diagrammatic view of the distal end of the duct housing a capillary.
Figure 7:
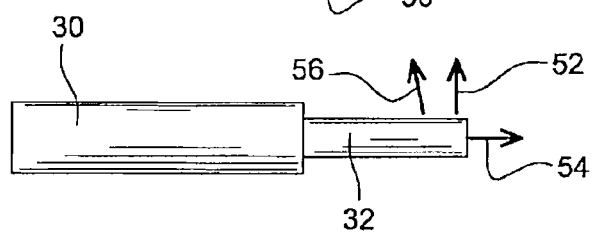
FIG. 7 is a diagrammatic view of the penetrant test material being sprayed.

The proximal end of the capillary 32 is connected to a supply of a given penetrant test material. The device may then be used with a plurality of capillaries 32, each of which is associated with a supply of a given penetrant test material. Each capillary has a spray endpiece at its distal end enabling the penetrant test material to be sprayed in a particular direction. The endpiece is advantageously removable and may be replaced at will with endpieces of other types suitable for performing spraying that is radial 52, forward 54, or backward 56 (FIG. 6).

Figure 8A:
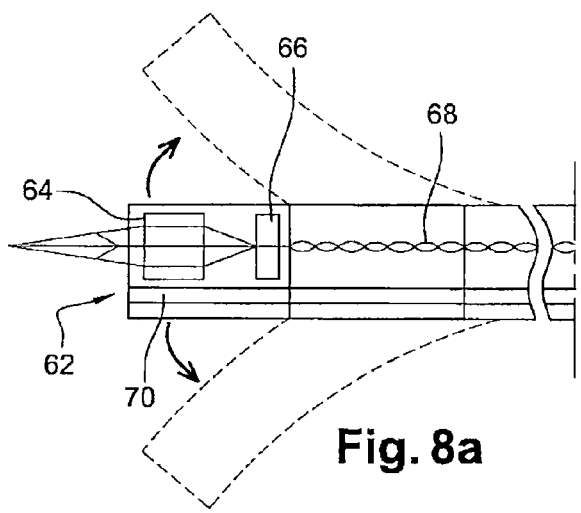
FIG. 8a is a diagrammatic section view of the distal end of the flexible sheath of the device of the invention.

The device includes image-taking means and image-transmission means as shown in FIG. 8a. The image-taking means comprise an image-forming lens 64 transmitting the image onto a camera 66 such as a charge-coupled device (CCD) camera having its output connected to an analog-to-digital converter. The digitized image is then transferred by a cable 68 to external display means such as a monitor of a computer processor system.

In a particular configuration of the device of the invention, the camera 66 has 500,000 pixels, each having a side lying in the range 8 micrometers ($\mu$m) to 12 $\mu$m.

The device also has second image-transmission means provided inside the sheath and comprising a set of optical components (not shown) transmitting the image formed by the lens to an eyepiece 58 carried by the proximal end of the handle.

The device also has light-guide means and illumination means extending to the proximal end of the sheath. By way of example, these means may comprise an optical fiber cable 70 extending from the distal end of the sheath to a connector 60 for coupling to a source of visible or ultraviolet light.

Figure 8B:
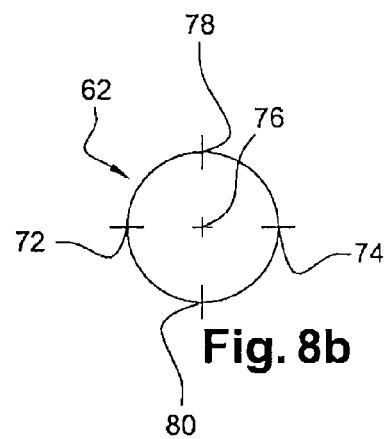
FIG. 8b is a diagrammatic view in section of the distal end of the examination head of the device of the invention.

In order to spray penetrant test materials in the proper direction towards the part and in order to observe the treated zone appropriately, the device includes means for adjusting the orientation of the examination head 62 (FIGS. 8a and 8b).

By way of example, these adjustment means comprise two cables that are guided inside the sheath and that have their distal ends fastened to the examination head 62 at two diametrically opposite points 72 and 74. The proximal portions of the cables are wound under tension in opposite directions on a rotary control member 76 of the handle (FIG. 2). Thus, by turning the control member 76 in a given direction, the examination head 62 can be tilted in a plane containing the two fastener points 72 and 74, and also the central axis 76 of the examination head.

It is possible to add two additional cables having their distal ends fastened to the examination head 62 at two diametrically opposite points 78 and 80 that are at 90° to the two fastener points 72 and 74 of the first two cables. The proximal portions of these two additional cables should likewise be wound onto a rotary member of the handle. With such an arrangement, it becomes possible to tilt the examination head 62 in two orthogonal planes, one of which contains the points 72 and 74 and the other of which contains the points 78 and 80, thereby enabling the distal end of the sheath to be oriented in four different directions.

Figure 9:
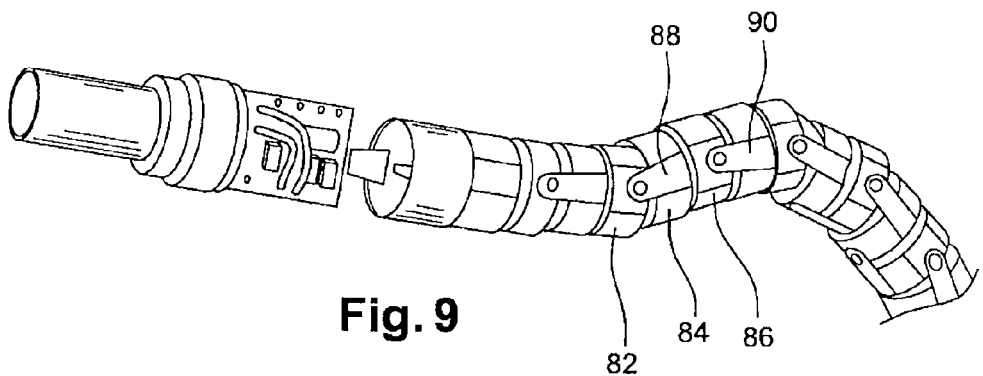
FIG. 9 is a perspective view of an orientable examination head of the device of the invention.

In order to enable the examination head 62 to be tilted, it may comprise non-touching metal annulus 82, 84, 86 (FIG. 9). An annulus 84 is connected to a downstream ring 82 by two blades 88 that are angularly spaced apart by 180°, being pivotally hinged on the outer periphery of the downstream annulus 82 and being fastened on the annulus 84 at 180° from each other. The annulus 84 is fastened to an upstream annulus 86 by two blades 90 that are likewise angularly spaced apart by 180°, and that are pivotally hinged at one end to the outer periphery of the annulus 84. The second ends of the two blades 90 are fastened on an upstream annulus 86 at 180° to each other. The blades 88 joining the annulus 84 to the downstream annulus 82, and the blades 90 joining the annulus 84 to the upstream annulus 86 are spaced apart at 90° from one another (FIG. 9).

Each annulus has four bridges (not shown) that are spaced apart at 90° in pairs for slidably guiding cables fastened to the distal end of the examination head 62. In a variant embodiment of the invention, the cables for controlling the orientation of the examination head are wound under tension on a motor-driven rotary member that may be housed in the handle.

Figure 10:
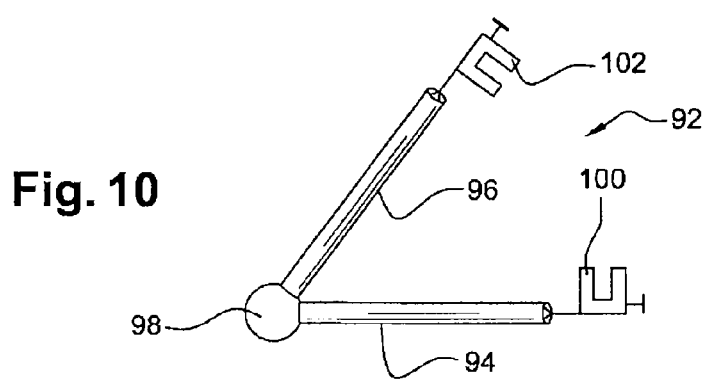
FIG. 10 is a diagrammatic view of an arm for holding the endoscope of the invention.

FIG. 10 shows an arm 92 for holding the handle of the endoscope. This holding arm 92 has two rods 94 and 96 that are pivotally hinged relative to each other at 98 at a first one of their ends. A respective clamp 100, 102 is pivotally hinged to the other end of each of the rods 94, 96. A first clamp 100 is for clamping onto the handle of the endoscope 36 and the other clamp 102 is for fastening on a portion of the turbine engine so as to enable the endoscope to be used in a static position.

In a variant embodiment of the invention (not shown), the means for feeding air under pressure are connected to a coupling leading with the rigid tube into a common cavity formed inside the handle, the proximal end of the duct leading to the inside of this cavity so as to allow the capillary inserted from the free end of the rigid tube to pass through and so as to allow the stream of air under pressure to flow to the distal end of the sheath. In this configuration, the endpiece has a single central orifice into which a capillary is inserted.

In a practical embodiment of the invention, the sheath 28 is of circular section with a diameter lying in the range 6 mm to 10 mm, the duct 30 for passing the capillary 32 has a diameter of about 1.2 mm, and the capillary 32 has a diameter of about 0.8 mm. The flexible sheath may have a length of about 1.5 meters (m).

In another embodiment of the invention, the sheath may be rigid and the capillary may be flexible or indeed rigid. Nevertheless, a rigid sheath in the form of a stick as in the prior art does not make it possible to take action in zones inside a turbine engine that are accessible only via passages that are curved or not rectilinear.

Thus, using a flexible sheath with a flexible capillary makes it possible to perform non-destructive testing of zones that are difficult to access without requiring the engine to be taken to a maintenance workshop, thereby reducing the time required for maintenance and the costs of operating the engine.

Reference is made below to FIGS. 11 to 19 which show other embodiments of the invention.

Figure 11:
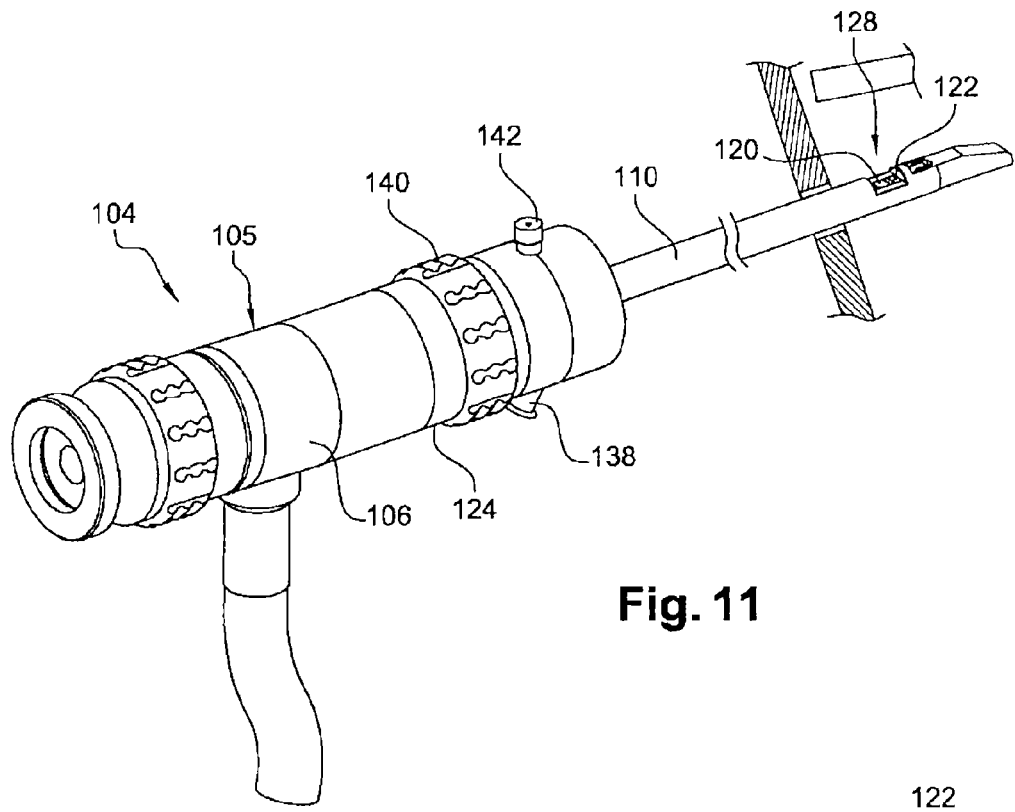
Figure 12:
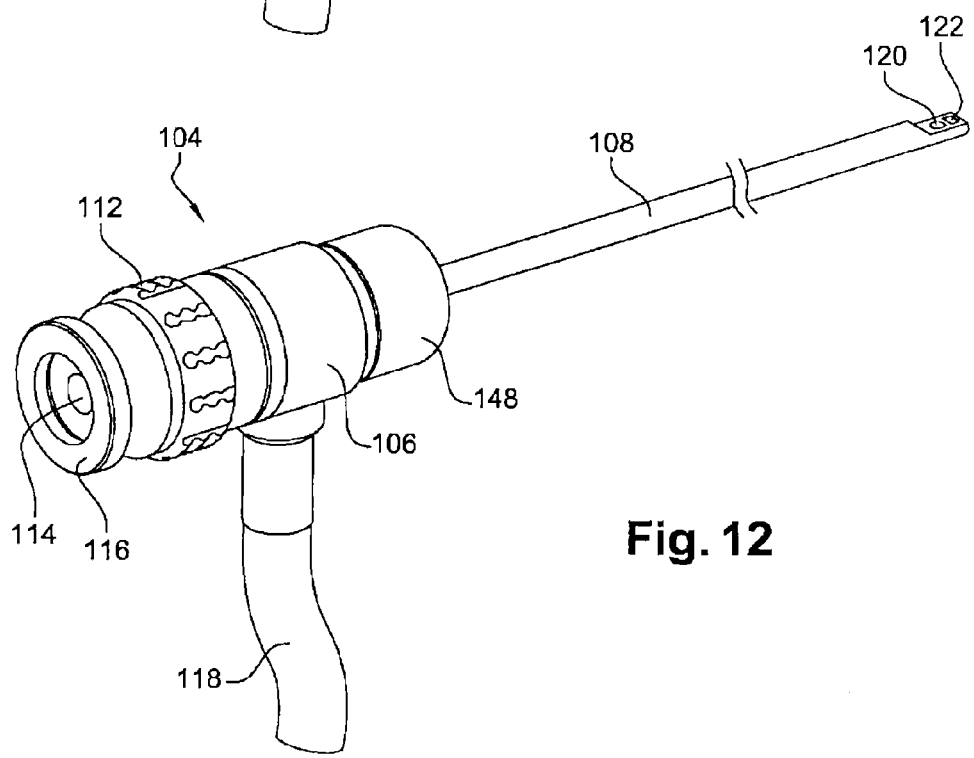

The endoscope 104 has a handle 105 with a proximal portion 106 and a distal portion 124, and a sheath forming a rigid distal inspection tube 108. In FIG. 11, the tube 108 is engaged in an inspection tube 110. The handle 106 has a focusing ring 112 and an eyepiece 114 housed in a proximal eyecup 116 suitable for being connected to an endoscopic camera. The endoscope 104 has a path for transmitting illumination light comprising a bundle of illumination fibers (not shown) extending in an illumination cable 118 secured to the handle 106. The distal portion of the tube 108 includes a porthole 120 at the distal end of an image optical path of the endoscope 104, and a window 122 behind which it is possible to stick the previously-polished distal end of the bundle of illumination fibers.

The endoscope has a tube 126 with a distal lateral opening 128 under which there are positioned the viewing window or porthole 120 and the illumination window 122 of the endoscope 104 (FIG. 11). The distal end of the tube 110 is secured to a hinge finger 130 having an internal channel 132 leading at one end to an orifice 134 and at an opposite end into a working channel or duct 136 housed in the tube 110. In the handle 124, the working channel 136 leads into a socket 138 leading to the proximal end of the working channel 124. The working channel 124 is designed to enable a flexible capillary tube 32 to be slidably inserted (FIG. 15), which tube can enter via the socket 138 and leave via the orifice 134. Such a capillary tube is for spraying penetrant test materials onto the part to be inspected. The handle 124 also has a control ring 140 making it possible to adjust the angle of the hinge finger 130 manually. The handle 124 may also have a socket 142 connectable to a source of compressed air, in communication with an air-blow tube 144 leading into the opening 128, parallel to the porthole 120 and the illumination window 122.

In FIGS. 13, 15, and 16, the distal portion 124 of the handle 105 includes a cylindrical proximal housing 146 for receiving the cylindrical distal end 148 of the proximal portion 106 of the handle 105 of the endoscope 104. The housing 146 has a distal partition 150 provided with an axial orifice constituting the proximal end of an internal cylindrical tube 152 for receiving the tube 108 of the endoscope 104. Means for assembling and fastening the handle 105 in the housing 146 may include an indexing and locking device (not shown) enabling the distal end of the tube 108 of the endoscope to be properly positioned under the distal opening 128 of the endoscope 104.

The distal portion 124 of the handle 105 has a proximal cylindrical part 154 with a proximal portion forming the cylindrical housing 146 and with a tubular distal portion 155 having a longitudinal slot 156.

The endoscope has a ring 140 for controlling the angle of the distal hinge finger 130. A cylindrical ring 158 is mounted stationary inside the control ring 140 and has a helical slot 160 formed in its periphery. A tubular couple 162 is slidably mounted around the internal tube 152 and has a radial finger 164 on its outer periphery. The shuttle 162 is secured to two longitudinal maneuvering rods 166, 168 extending inside the tube 126 and serving to control the angle of the distal hinge finger 130.

The control ring 140 and the cylindrical ring 158 are mounted around the tubular distal portion 155 of the proximal cylindrical part 154. The tubular shuttle 162 is mounted inside the tubular distal portion 155 of the proximal cylindrical part 154 and the radial finger 164 passes through the longitudinal slot 156 of the tubular distal portion 155 of the proximal cylindrical part 154, and its radially outer end is received in the helical slot 160 of the cylindrical ring 158.

The distal portion 124 of the handle 105 also has a central part 170 and a distal part 172 which in association with the proximal cylindrical part 154 serves to block movement in translation of the distal portion 124 of the handle 105 and the cylindrical ring 158 around the tubular distal portion 155 of the proximal cylindrical part 154, while forming two lateral orifices that allow sockets 138 and 142 to pass and be fastened. The parts 154, 170, and 172 can thus be secured, e.g. by means of two screws 174a, 174b that are engaged in orifices provided for this purpose in the part 172 and that are screwed into the part 154.

In operation, turning the control ring 140 about the tubular distal portion 155 of the proximal cylindrical part 154 causes the radial finger 130 to move in translation in the longitudinal slot 156, thereby causing the tubular shuttle 162 to move axially.

The distal portion of the tube 124 has a distal part 176 comprising:
  a proximal tubular cylindrical portion 178 with an internal orifice 180 provided for receiving the distal end of the internal tube 152;
  a middle tubular housing 182 presenting a lateral opening 128 and a distal partition 184, the housing 182 being designed to receive the distal end of the tube 108 of the endoscope 104 inserted into the internal tube 152;
  two distal longitudinal lugs 186, each having a transverse orifice 188;
  a longitudinal channel with a proximal end that receives the blow tube 144 and a distal end leading to the housing 182;
  a longitudinal channel having a proximal end that receives the working channel 136 and having a distal portion leading to between the two lugs 186; and
  two longitudinal channels leading to between the two distal lugs 186 and slidably receiving the maneuvering rods 166 and 168.

The distal portion of the internal part 176 is associated with an internal pulley 190 having an axial orifice 192 perpendicular to the axis of the tube 126 and an annular groove 194 provided for guiding the capillary tube 32 inserted into the working channel 136 via the socket 138. The hinge finger 130 has two lugs 196 at its proximal end, each lug presenting a distal transverse orifice 198 and a proximal transverse orifice 200.

The part 176, the pulley 190, and the hinge finger 130 are assembled together by a cylindrical pin 202 passing successively through the orifice 188 in one of the distal lugs 186 of the part 176, the orifice 198 in one of the proximal lugs 196 of the finger 130, the orifice 192 in the pulley 190, the orifice 198 in the other proximal lug 196, and finally the orifice 188 in the other distal lug 186 of the part 176.

The hinge finger 130 is assembled with the maneuvering rods 166 and 168 separately for each of the rods with the help of a respective transverse cylindrical pin 204 inserted into the proximal orifice 200 of one of the two lugs 196 of the finger 130, and then in an orifice 206 provided at the distal end of the corresponding maneuvering rod 166, 168.

In operation, the finger 130 can thus be tilted and positioned angularly between an axial position in which it is in alignment with the axis of the tube 126 (FIG. 13) and a position in which it is oriented perpendicularly to the axis of the tube 126 (FIG. 14).

A capillary tube 32 can be inserted into the working channel 136 and then into the channel 132 while the hinge finger 130 is in its axial position. The positioning of the distal outlet from the capillary 32 on the part for inspection is performed by turning the control ring 140 so as to orient the finger 130 towards a direction that is perpendicular to the axis of the tube 126 with the length of the distal portion of the capillary tube 32 that projects beyond the finger 130 being adjusted under visual monitoring with the help of the endoscope 104.

FIGS. 18 and 19 show a flexible video endoscope probe adapted to penetrant testing under illumination by ultraviolet (UV) light, and adapted to accessing internal zones of a turbine engine.

The video endoscope probe has a control handle with a distal end that is secured to a flexible inspection tube 208, and a proximal end that is generally secured to an umbilical cable (not shown) enabling the probe to be connected to operating devices, such as a light generator.

For penetrant testing, the control handle of the probe is fastened to a specific part 210 having a distal end secured to a distal sleeve 212. The part 210 is a tubular part having an axial proximal housing within which the control handle is fastened. The part 210 has an oblique lateral tubular inlet 216 with an outside end that presents internal tapping 214.

The sleeve 212 may be made of a flexible material, and it surrounds the proximal end of the inspection tube 208. The inspection tube 208 includes a flexible distal angulation 218 and a distal examination head 220 housing an optoelectronic device having illumination means and image-taking means analogous to those described with reference to FIGS. 8a and 8b. A nut ring 222 is fastened on an outside thread 224 at the distal axial end of the part 210 in order to secure the part 210 in leaktight manner with the sleeve 212.

The part 210 has an axial tubular channel 226 housing the following connections:
  a bundle of illumination fibers 228;
  four flexible sheaths 230; and
  a multiconductor electric cable 232.

The bundle of illumination fibers 228 connects an axial illumination window 234 situated on a distal face of the distal head 220 without discontinuity to the proximal end of the umbilical cable of the video endoscope probe. The proximal end of the umbilical cable may be connected to an illumination generator suitable for delivering equally well white light or UV light.

The four sheaths 230 are designed to guide four flexible control cables whose distal ends are secured to the distal angulation 218 and whose proximal ends are actuated by a manual or motor-drive control member, which may be housed in the control handle. The control cables and the control member may be similar to those described with reference to FIGS. 8b and 9.

The multiconductor electric cable 232 connects the image sensor housed in the distal head 220 to a video processor that may be housed in the control handle. The main functions of the video processor are to synchronize the distal image sensor and to transform the electric signal delivered by the sensor into a standardized video signal. The image sensor is associated with a lens 235 forming a viewing window that is likewise located in the distal face of the head 220.

The oblique tubular inlet 216 of the part 210 is designed to receive the proximal portion 236 of a working channel or duct, which proximal portion is fastened in the oblique tubular inlet 216, e.g. by adhesive. The proximal portion 236 may be made of a rigid material, e.g. a metal. The distal end of the proximal portion 236 of the working channel is secured (with the help of a releasable device for maintenance purposes that is not shown) to the proximal end of a flexible proximal portion 238 of the working channel as received in the inspection tube 208. The distal end 238 of the proximal portion of the working channel leads to an orifice 241 formed in the distal face of the distal head or examination head 220 (FIG. 5A).

The distal end of an intermediate tubular part 240 is screwed (or adhesively bonded) in the oblique tubular inlet 216 of the part 210 by means of a distal outside thread.

A coupling part 246 including a lateral inlet 242 and a proximal axial inlet may be associated in leaktight manner with the part 240 by means of a ring 244 screwed onto the periphery of the intermediate part 240 and held axially against an annular rim of the coupling part. A sealing 0-ring is clamped at the interface between the coupling part 242 and the intermediate tubular part 240. The proximal axial inlet of the coupling part 246 presents a diameter that is slightly greater than the diameter of a flexible capillary 32 suitable for being inserted therein. The proximal axial inlet of the part 246 may be fitted with a removable sealing cap 248 made of a flexible material and presenting an axial orifice into which the operator can insert a capillary tube 32 that is capable of sliding in the working channel 236, 238 until its distal portion emerges from the orifice 241 in the distal face of the distal head 220. The lateral inlet 242 of the part 246 is connected to means for feeding air under pressure. Under such conditions, the air injected via the inlet 242 flows in the annular space between the outside surface of the capillary tube 32 and the inside surface of the working channel 236, 238 until it exits via the orifice 241 in the distal head 220. In this way, the air as injected in this way via the inlet 242 can prevent the penetrant test materials sprayed by the remote outlet of the capillary tube 32 from becoming deposited on the viewing window 235 and the illumination window 234 on the distal face of the head 220, thereby serving to clean these windows. The air injected into the working channel also avoids the working channel being polluted by drops of the penetrant test material.

The ability to disconnect the coupling device 246 directly constitutes an important advantage in terms of maintenance, insofar as it makes it easier to clean the working channel 236, 238 periodically.

In another embodiment, the illumination device of the video endoscope probe may comprise at least two light-emitting diodes (LEDs), one emitting white light and the other emitting UV light, these two LEDs being installed in the distal end of the probe.

In embodiments that include a bundle of illumination fibers, the bundle of illumination fibers may be replaced by a liquid light guide suitable for transmitting UV light and white light, or it may be associated with such a liquid light guide that may be removable.

It can clearly be seen by the person skilled in the art that the present invention may be subjected to a wide variety of embodiments and applications. In particular, the above-described video endoscope probe may include an air-blow tube that is distinct from the working channel and that leads to the distal head 220 of the probe so as to deliver air onto the illumination and viewing windows.

The endoscope of the invention may be used with inspection tubes that are flexible or rigid. In an endoscope or a video endoscope having a flexible inspection tube fitted with a distal angulation, the viewing and illumination windows may be lateral or axial. When these windows are axial, the tube 126 has an opening enabling these windows to be oriented laterally with the help of the angulation. When the windows are lateral, the angulation may be omitted.

In the various embodiments of the invention as described above, the illumination fibers are made of a material suitable for transmitting both visible light and UV light, e.g. they are made of quartz or of a polymer that is suitable for transmitting both white light and UV light.

By blowing air over the illumination means and the image-taking means, there is no need at any time to remove the inspection tube from the endoscopic inspection orifice, in particular during or after spraying penetrant test materials onto the part for inspection, and the tube can remain in place until the end of visually inspecting the part under illumination with UV light, thereby reducing the time needed for endoscopic inspection operations.

Injecting air into the working channel 236, 238 while injecting penetrant test materials, in combination with the fact that the capillary tube immerses from the distal end of the working channel, contributes to greatly reducing the amount of pollution both in the working channel and on the examination head.

It may be preferable to avoid mixing penetrant test materials. Under such circumstances, a different capillary tube 32 may be used for injecting each penetrant test material. The capillary tubes that are used may thus be single-use tubes.

The invention claimed is:

1. A device for searching for defects on parts that are masked and accessible via a passage that is not rectilinear inside a turbine engine, or on an airplane turboprop or turbojet, the device comprising:
    a tubular sheath;
    a duct housed inside the sheath;
    light-guide means for guiding light;
    image-transmission means for transmitting images housed in the sheath to illuminate and observe a part for inspection;
    an examination head at a distal end of the sheath, the head including illumination means and image-taking means connected to the light-guide means and to the image-transmission means housed in the sheath;
    means for spraying a succession of penetrant test materials on the part for inspection, comprising a capillary slidably guided inside the duct housed inside the sheath;
    means for adjusting an orientation of the examination head at the distal end of the sheath; and
    air-blow means for blowing air on the illumination means and on the image-taking means located at the distal end of the sheath.

2. A device according to claim 1, wherein the air-blow means comprises means for feeding air under pressure that are connected to a blow tube leading at its distal end to a vicinity of the illumination means and the image-taking means.

3. A device according to claim 2, wherein the means for feeding air under pressure is connected to a proximal end of the duct for passing the capillary to feed the duct with a continuous stream of air that leaves via its distal end.

4. A device according to claim 1, wherein a proximal end of the sheath is connected to a handle for fastening to the engine, and the duct housing the capillary is extended inside the handle and is connected to a rigid tube carried by the handle and serving to insert the capillary into an inside of the duct.

5. A device according to claim 4, further comprising holder means for preventing the capillary from sliding inside the duct.

6. A device according to claim 5, wherein the holder means comprises an endpiece including means for clamping onto the capillary and configured to be engaged and held on a free end of the rigid tube.

7. A device according to claim 6, wherein the endpiece includes a passage leading to an inside of the tube and forming an inlet for connection to a means for feeding air under pressure.

8. A device according to claim 4, wherein the orientation adjustment means comprises a control member for controlling angular orientation of the examination head, which member is rotatably mounted on the handle and is connected to transmission means for transmitting the orientation control to the examination head, the transmission means being housed in the sheath.

9. A device according to claim 7, wherein the means for adjusting the orientation of the examination head comprises at least two cables guided inside the sheath and fastened at their distal ends to the examination head at two diametrically opposite points, and wound under tension at their proximal portions in opposite directions on a rotary control member situated on the handle.

10. A device according to claim 8, wherein the means for transmitting the orientation control comprises at least one rod extending inside the sheath and connected at its distal end to a mechanism for converting rotary movement of a ring into movement in translation of the rod, the rod being connected by its distal end to a finger that is pivotally hinged to the distal end of the sheath about an axis that is perpendicular to the sheath.

11. A device according to claim 10, wherein the distal finger includes an axial channel for passing the capillary and is hinged to pivot between a position in which it is in alignment with an axis of the sheath and a position in which it is oriented perpendicularly to the axis of the sheath.

12. A device according to claim 1, wherein the tubular sheath is flexible, and the capillary is flexible.

13. A device according to claim 1, wherein the distal end of the sheath includes a spray endpiece at its distal end.

14. A device according to claim 13, wherein the spray endpiece at the distal end of the capillary is removable and can be selected from a set of spray endpieces for spraying radially, forwards, or backwards.

15. A method of non-destructive penetrant testing of a part that is masked, by using a device according to claim 1, the method comprising:

inserting and guiding the examination head inside a three-dimensional structure to a position for examining the part for inspection;

with the examination head placed facing the part for inspection, feeding the proximal end of the capillary with a first penetrant test material and applying the first material via the distal end of the capillary to the part for inspection;

slidably withdrawing the capillary from the duct in which the capillary is housed; and slidably inserting a second capillary into the duct and bringing a distal end thereof into a vicinity of the part for inspection, and then feeding the proximal end of the second capillary with a second penetrant test material and applying the second material via the distal end to the part for inspection.

16. A device for searching for defects on parts that are masked and accessible via a passage that is not rectilinear inside a turbine engine, or on an airplane turboprop or turbojet, the device comprising:

a tubular sheath;

a duct housed inside the sheath;

light-guide means for guiding light;

image-transmission means for transmitting images housed in the sheath to illuminate and observe a part for inspection;

an examination head at a distal end of the sheath, the head including illumination means and image-taking means connected to the light-guide means and to the image-transmission means housed in the sheath;

means for spraying a succession of penetrant test materials on the part for inspection, comprising a capillary slidably guided inside the duct housed inside the sheath and that can be removed from the duct;

means for adjusting an orientation of the examination head at the distal end of the sheath; and air-blow means for blowing air on the illumination means and on the image-taking means located at the distal end of the sheath.

* * * * *